United States Patent

Waycott et al.

[11] Patent Number: 5,973,232
[45] Date of Patent: Oct. 26, 1999

[54] *LACTUCA SATIVA* CULTIVAR EXHIBITING RESISTANCE TO DOWNY MILDEW AND CORKY ROOT ROT

[75] Inventors: William Waycott, San Luis Obispo; Dean Charles Gregg, Salinas; Keith Trammell, Nipomo, all of Calif.

[73] Assignee: Seminis Vegetable Seeds, Inc., Saticoy, Calif.

[21] Appl. No.: 08/986,624

[22] Filed: Dec. 8, 1997

[51] Int. Cl.⁶ .............................. A01H 5/00; A01H 5/10; A01H 1/04

[52] U.S. Cl. .................... 800/305; 800/260; 800/265; 800/301

[58] Field of Search ..................... 800/260, 265, 800/301, 305

[56] References Cited

U.S. PATENT DOCUMENTS 5,684,226  11/1997  Sarreal ..................................... 800/200

OTHER PUBLICATIONS

Research Project Report to the California Iceberg Lettuce Advisory Board's research Program for the period of Apr. 1, 1992–Mar. 31, 1993, van Bruggen et al., pp. 91–99.

Variation in California Population of Lettuce Downy Mildew in 1995. Published in the Iceberg Lettuce Advisory Board Annual Report Apr. 1, 1995–Mar. 31, 1996, California Iceberg Lettuce Advisory Board, 512 Pajaro Street, Salinas, CA 93901, Michelmore et al., pp. 44–54.

Lettuce Production In the United States, Published by The Agricultural Research Service United States Department of Agriculture (1974).

Guide to Leafy Vegetable Production In the Far West, Ron Smith, ed., *California Arizona Farm Press* (1997).

Ryder, E.J. Leafy Salad Vegetables, *AVI Publishing Company*, 1979, pp. 13–94.

1995 Imperial County Agricultural Crop & Livestock Report.

1995 Monterey County Crop Report The Year of The Flood.

1996 California Agricultural Resource Directory, California Department of Food and Agriculture.

1996 Monterey County Crop Report, Agricultural Comm. Richard W. Nutter.

From Field to Table, Agriculture Comm. Richard D. Greek, 1995 Annual Report.

Santa Barbara County Agricultural Commissioner, 1995 Production Report.

*Primary Examiner*—David T. Fox
*Attorney, Agent, or Firm*—Rockey Milnamow & Katz, Ltd.

[57] ABSTRACT

The present invention relates to a new crisphead *Lactuca sativa* cultivar, designated Sharp Shooter, which exhibits resistance to downy mildew pathotypes I, IIA, III, and IV and corky root rot pathotype CA1, a color of 146A according to The R.H.S. Colour Chart published by the Royal Horticultural Society of London, England, and mature heads of which weigh about 10% to about 40% more than comparable varieties of crisphead lettuce.

4 Claims, No Drawings

LACTUCA SATIVA CULTIVAR EXHIBITING RESISTANCE TO DOWNY MILDEW AND CORKY ROOT ROT

TECHNICAL FIELD OF THE INVENTION

The present invention relates to a new *Lactuca sativa* variety that exhibits resistance to downy mildew and corky root rot.

BACKGROUND OF THE INVENTION

Lettuce is unique among the major vegetables in its nearly exclusive use as a fresh, raw product. It is rarely found far from a salad or sandwich. It is occasionally used as a cooked vegetable and has even been used as a substitute for tobacco in cigarettes. Ryder, E. J., *Leafy Salad Vegetables*, AVI Publishing Company, pgs. 15–16 (1979).

Lettuce is in the Cichoreae tribe of the Asteraceae (Compositae). Id. at 22. Its Latin name is *Lactuca sativa* L. Lettuce is related to chicory, sunflower, aster, dandelion, artichoke, and chrysanthemum. Id. at 22–23. It is one of about 300 species in the genus Lactuca (milk-forming). Id. at 23. Cultivated lettuce is closely related to common wild lettuce, *L. serriola* Torner. Id.

There are six morphological types of lettuce: crisphead (iceberg), butterhead, cos (romaine), leaf, stem, and Latin. Id. at 47. The crisphead type is the most common in the United States, while butterhead and romaine types are popular in northern and southern Europe. Id. In the United States, California is the leading producer of lettuce. California produces crisphead, leaf and romaine lettuce. In 1995, California's cash receipts for crisphead lettuce amounted to about $987 million dollars. 1996 *California Agricultural Resource Directory*. Furthermore, also in 1995, California exported about $154 million dollars of crisphead lettuce to other countries such as Japan, Canada, the European Union, and Korea. Id.

Lettuce cultivars are susceptible to a number of diseases such as downy mildew, sclerotinia rot, botrytis, powdery mildew, anthracnose, bottom rot, corky root rot, lettuce mosaic virus, big vein, beet western yellows, and aster yellows, just to name a few. This diseases result in millions of dollars of lost lettuce crop throughout the world every year.

Downy mildew is a highly destructive diseases of lettuce grown at relatively low temperature and high humidity. Ryder, E. J., *Leafy Salad Vegetables*, AVI Publishing Company, p. 52 (1979). Downy mildew is caused by a fungus, *Bremia lactacae* Reg. Pale angular yellow areas bounded by veins appear on the upper leaf surfaces. Id. Sporulation occurs on the opposite surface. Id. The lesions eventually turn brown, and they may enlarge and coalesce. Id. The symptoms occur first on the lower leaves, but under ideal conditions may move into the upper leaves of the head. Id. When this happens, the head cannot be harvested. Id. Less severe damage requires the removal of more leaves than usual, especially at the destination. Id. In California, seven pathotypes of *Bremia lactucae* have been identified: Pathotype I, IIA, IIB, IIC, III, IV and V. (Michelmore, R. W., et al. 1996. *Variation in California Populations of Downy Mildew in* 1995. In Iceberg Lettuce Advisory Board Annual Report. California Iceberg Lettuce Research Advisory Board, Salinas, Calif. p.44–57). In addition to these major groupings of Bremia strains, many other novel isolates have been found throughout the State.

Corky root rot is believed to be caused by a species of Rhizomonas. One species of Rhizomonas that is commonly found to cause corky root rot is *Rhizomonas suberifaciens*. Corky root rot symptoms include yellow bands on tap and lateral roots of lettuce seedlings. Guide to Leafy Vegetable Production In the Far West, Ron Smith, ed., California-Arizona Farm Press (1997). Yellow areas gradually expand and develop a green-brown color and develop cracks and rough areas on the surface area of the root. Id. The entire tap root may become brown, severely cracked and may cease to function. Id. Feeder root systems are reduced and damaged. Id. Roots become very brittle and break off easily. Id. Internal discoloration of the root may occur. Id. When the root is severely discolored, above-ground symptoms show up as wilting during warm temperatures, stunting and general poor, uneven growth. Id. In California, several strains of *Rhizomonas suberifaciens* have been identified. However, only strain CA1 has been shown to cause damage to roots of plants grown in commercial lettuce production areas.

There is a need in the art for improved lettuce varieties that exhibit resistance to both downy mildew and corky root rot, and exhibit vigorous growth, and increased weight and yield.

SUMMARY OF THE INVENTION

The present invention relates to a new crisphead *Lactuca sativa* cultivar referred to as Sharp Shooter. Sharp Shooter exhibits vigorous growth and resistance to downy mildew pathotypes I, IIA, III, and IV and corky root rot pathotype CA1. In addition, Sharp Shooter has a color of 146A according to the R.H.S. Colour Chart published by the Royal Horticultural Society of London, England. Furthermore, Sharp Shooter weighs from about 10% to about 40% greater than a comparable crisphead *Lactuca sativa* cultivar. Specifically, mature heads of Sharp Shooter weigh from about 820.0 grams to about 960.0 grams, preferably about 890 grams. Seeds of Sharp Shooter have been deposited with the American Type Culture Collection (ATCC) in Rockville, Md. and have been assigned ATCC Accession No. 209461.

The present invention also relates to a *Lactuca sativa* plant produced by growing the seed of Sharp Shooter that have ATCC Accession number 209461. The present invention also relates to a *Lactuca sativa* plant that has all the physiological an morphological characteristics of a *Lactuca sativa* plant grown from seed of ATCC Accession No. 209461.

Finally, the present invention relates to a $F_1$ hybrid *Lactuca sativa* plant having Sharp Shooter as a parent.

DETAILED DESCRIPTION OF THE INVENTION

The present invention relates to a novel crisphead Lactuca sativacultivar, named Sharp Shooter, that exhibits resistance to downy mildew and corky root rot. More specifically, the lettuce cultivar of the present invention exhibits resistance to downy mildew pathotypes I, IIA, III and IV and corky root rot pathotype CA1. Furthermore, the cultivar of the present invention exhibits increased weight and increased number of plants harvested over comparable crisphead *Lactuca sativa* varieties. As used herein, a "comparable crisphead *Lactuca sativa* varieties" refers to *Lactuca sativa* varieties that are resistant to corky root rot. "Comparable *Lactuca sativa* varieties" are capable of growing in corky root rot infected soils. Specifically, the cultivar of the present invention weighs from about 10% to about 40% greater than a comparable variety of crisphead *Lactuca sativa*. More specifically, mature heads of the cultivar of the present invention weigh from about 820.0 grams to about 960.0 grams, preferably about 890.0 grams.

The cultivar of the present invention was developed as follows. In 1986, the crisphead lettuce cultivar Montello was crossed as the female parent with the crisphead lettuce cultivar El Toro as the male parent using traditional cross hybridization techniques. Montello is a public variety that has been released jointly by the Wisconsin Agricultural Experiment Station and the U.S. Department of Agriculture and is known to be a source of corky root rot resistance. Seed of Montello is available from the United States Department of Agriculture, ARS, 1636 East Alisal Street, Salinas, Calif. 93905. El Toro is commercially available from Harris Moran Seed Company (Harris Moran Seed Company 100 Breen Road, San Juan Baustista, Calif.) and is known to be a source of vigorous growth. Also in 1 986, the resulting $F_1$ seed from the cross was collected, planted, and allowed to self-pollinate. The resulting $F_2$ seed was collected. In 1987, the $F_2$ seed was planted. From the resulting plants, 11 plants were selected. The selection criteria for these plants was vigorous and cool season performance (from the parent El Toro) combined with corky root rot resistance (from the parent Montello). These 11 plants were allowed to self-pollinate and the resulting $F_3$ seed collected. In 1 988, the $F_3$ seed was planted. From the resulting plants, a single plant was selected using the same selection criteria employed for the selection of the $F_2$ plants. This plant was allowed to self-pollinate and the resulting $F_4$ seed collected. In 1989, the $F_4$ seed was planted. From the resulting plants, 4 plants were selected using the same selection criteria employed for the selection of the $F_2$ and $F_3$ plants. The 4 plants were then self-pollinated and the resulting $F_5$ seed was collected.

In 1990, the $F_5$ seed was planted. The resulting plants were used as female parents and crossed with the crisphead lettuce cultivar Alpha, using traditional cross hybridization techniques. Alpha is commercially available from Harris Moran Seed Company and is a source of downy mildew resistance genes DM 1 and DM 5/8. The resulting $F_1$ seed from this cross was then collected. In 1991, the $F_1$ seed was planted and self-pollinated and the resulting $F_2$ seed was collected. In 1991, the $F_2$ seed was planted. From the resulting plants, 62 plants were selected. The selection criteria for these plants was vigorous, cool season performance and corky root rot resistance from the cross (El Toro by Montello) and downy mildew resistance (from the parent Alpha). These 62 plants were allowed to self-pollinate and the resulting $F_3$ seed was collected. In 1992, the $F_3$ seed was planted. From the resulting plants, 10 plants were selected. These plants were selected using the same selection criteria employed for the selection of the $F_2$ plants. These 10 plants were allowed to self-pollinate and the resulting $F_4$ seeds collected. In 1 993, the $F_4$ seeds were planted. From the resulting plants, 3 plants were selected. The selection criteria was the same as the criteria employed for the selection of the $F_2$ and $F_3$ plants. These 3 plants were allowed to self-pollinate and the resulting $F_5$ seed collected. In 1994, the $F_5$ seed was planted. From the resulting plants, 21 plants were selected. The selection criteria was the same as the criteria employed for the selection of the $F_{2-F4}$ plants. The 21 plants were allowed to self-pollinate. The resulting $F_6$ seed was collected. In 1995, the $F_6$ seed was planted and from the resulting plants, 15 plants that were judged uniform were selected and bulked for trailing and seed increase. The selection criteria was the same as the criteria used to select the $F_{2-5}$ plants. The resulting $F_7$ seed was coded Sharp Shooter. The $F_7$ seed was planted and the resulting plants bulked for further trialing and seed increase. The resulting $F_8$ seed was collected.

Seeds of Sharp Shooter developed as a result of the above breeding have been deposited under the Budapest Treaty with the American Type Culture Collection (ATCC), 10801 University Boulevard, Manassas, Va. 20110-2209 on Nov.14, 1997 and have received Accession number 209461. This deposit of Sharp Shooter will be maintained in the ATCC depository, which is a public depository, for a period of 30 years, or 5 years after the most recent request, or for the enforceable life of the patent, whichever is longer, and will be replaced if it becomes nonviable during that period. Additionally, Applicant has satisfied all the requirements of 37 C.F.R. Sections 1.801–1.809, including providing an indication of the viability of the sample. Furthermore, a Plant Variety Protection Certificate has been applied for with the United States Department of Agriculture.

The present invention further contemplates a *Lactuca sativa* plant produced by growing the seed of Sharp Shooter that has ATCC Accession No. 209461. Additionally, the present invention also contemplates a *Lactuca sativa* plant that has all of the physiological and morphological characteristics of Sharp Shooter.

Finally, the present invention contemplates a $F_1$ hybrid *Lactuca sativa* plant that has Sharp Shooter as one of its parents.

As discussed earlier, Sharp Shooter exhibits resistance to downy mildew and corky root rot. More specifically, Sharp Shooter exhibits resistance to downy mildew pathotypes I, IIA, III and IV as well as corky root rot pathotype CA1. Sharp Shooter has a color of 146A according to the R.H.S. Colour Chart published by the Royal Horticultural Society of London, England. Additionally, mature heads of Sharp Shooter weigh from about 820.0 grams to about 960.0 grams, preferably about 890.0 grams. Finally, Sharp Shooter yields from about 1 55.0 to about 195.0, preferably about 175.0, plants per 200 plants.

Sharp Shooter is a vigorous cultivar that has a healthy root system. The healthy root system is a result of the cultivar's resistence to corky root rot. More specifically, Sharp Shooter has a root system with a high root mass. Typically, crisphead *Lactuca sativa* cultivars that are susceptible to corky root rot have a root system that has a low root mass. Because of this low root mass, such cultivars require frequent watering, specifically, 3 to 4 irrigation's after thinning, in order to prevent them from drying out and having a small head size.

Additionally, Sharp Shooter is less vulnerable to attack by sclerotinia than other crisphead lettuce varieties. Sclerotinia is a fungus that attacks most vegetables and is typically found in vegetable plants where the soil moisture is high, particularly where overhead irrigation is used. The inventors of Sharp Shooter believe that the reason Sharp Shooter exhibits less sclerotinia is because this variety does not require as much irrigation as other crisphead varieties due to of its high root mass.

The inventors of the present invention further believe that plant habit may also play a role in Sharp Shooter exhibiting less sclerotinia. The frame (outside leaves) leaves of Sharp Shooter are upright and have minimal soil contact. The frame leaves of most crisphead lettuce cultivars are on the ground during most of the growing period and retain moisture which makes for an ideal environment for sclerotinia.

The closest comparable commercially available cultivars to Sharp Shooter are Premier and Bronco. Premier is commercially available from Harris Moran Seed Company. Bronco is commercially available from Coastal Seed Company (Coastal Seed Company, 1352 Burton Avenue, Salinas, Calif. 93901).

Premier is a crisphead lettuce cultivar that is resistant to downy mildew pathotypes I and IIA and corky root rot pathotype CA1. Premier has a color of 146A according to The R.H.S. Colour Chart published by The Royal Horticultural Society of London, England. In addition, mature heads of Premier weigh from about 618.0 grams to about 736.0 grams and yields from about 1 15.0 to about 160.0 plants per 200 plants sown.

Bronco is a crisphead lettuce cultivar that is resistant to downy mildew pathotypes I, IIA, III, and IV and corky root rot pathotype CA1. Bronco has a color of 146B according to The R.H.S. Colour Chart published by The Royal Horticultural Society of London, England. Mature heads of Bronco weigh from about 569.0 grams to about 710 grams and yields from about 93.0 to about 139.0 plants per 200 plants sown.

As shown above, mature heads of Sharp Shooter weigh about 10% to about 40% more than either Premier and Bronco and exhibits an increased yield over both of these cultivars.

The following Examples illustrate the preferred embodiments of the present invention and are not limiting of the specification and claims in any way.

EXAMPLE 1

Characteristics of Sharp Shooter

*Lactuca sativa* cultivar Sharp Shooter has the following morphologic and other characteristics:

Variety Description Information

Plant Type: Vanguard type lettuce
Seed:
  Seed Color: black (gray brown)
  Light Dormancy: Light is not required
  Heat Dormancy: Not susceptible
Cotyledons:
  Shape of Cotyledons: Intermediate
  Shape of Fourth Leaf: Obovate
  Length/Width Index of Fourth Leaf: (L/W×10)=17
  Apical Margin: Moderately Dentate
  Basal Margin: Incised
  Undulation: Flat
  Green Color: Medium Green
  Anthocyanin:
  Distribution: Absent
  Rolling: Absent
  Cupping: Uncupped
  Reflexing: None
Mature Leaves:
Margin:
  Incision Depth (Deepest penetration of the margin): absent/shallow (like Dark Green Boston which is commercially available under the Asgrow Brand from Seminis Vegetable Seeds, Inc., the assignee of the present invention).
  Indentation (Finest Division of the Margin): shallowly dentate (like Great Lakes 55. Seed of Great Lake 55 is available from the United States Department of Agriculture ARS, 1636 East Alisal Street, Salinas, Calif. 93905).
  Undulation of the Apical Margin: Absent/Slight (like Dark Green Boston)
  Green Color: Dark Green (Vanguard)

Anthocyanin (Grown at or below 10° C.):
  Distribution: Absent
  Size: Large
  Glossiness: Dull (Vanguard—Seed of Vanguard is available from the United State Department of Agriculture, ARS, 1636 East Alisal Street, Salinas, Calif. 93905).
  Blistering: Absent/Slight (Salinas—Seed of Salinas is available from the United States Department of Agriculture, ARS, 1636 East Alisal Street, Salinas, Calif. 93905).
  Leaf Thickness: Medium
  Trichomes: Absent (Smooth)
Plant
  Sharp Shooter Spread of Frame Leaves: 44 cm
  Bronco (comparison variety): 49 cm
  Head Diameter (market trimmed with single cup leaf)
  Sharp Shooter: 18 cm
  Bronco: 17 cm
  Head Shape: Spherical
  Head Size Class: Large, greater than 200mm in diameter
  Head Count per Carton: 24
  Head Weight: 887 grams
    Sharp Shooter: 887 g
    Bronco: 638 g
  Head Firmness: Very firm
  Butt: (Bottom of Market-trimmed Head)
    Shape: Rounded
    Midrib: Moderately Raised
  Core (Stem of Market-trimmed Head)
    Diameter at the base of the Head: 34 mm
    Ratio of Head Diameter/Core Diameter: 5.8
    Core Height from base of Head to Apex
      Sharp Shooter: 44 mm
      Bronco (comparison variety): 45 mm
  Bolting—First Water Date May 20, 1996.
  (Note: The first water date is the date the seed first receives adequate moisture to germinate. This can and often does equal the planting date).
    Number of Days from First Water Date to Seed Stalk
      Emergence (Summer condition):
      Sharp Shooter: 89 days
      Bronco: 87 days
    Bolting Class: Medium
    Height of Mature Seed Stalk:
      Sharp Shooter: 108 cm
      Bronco: 11 5 cm
    Spread of Bolter Plant:
      Sharp Shooter: 56 cm
      Bronco: 59 cm
  Bolter Leaves: Curved
  Margin: Dentate
  Color: Medium Green
  Bolter Habit
    Terminal Inflorescence: Present
    Lateral Shoots (above head): Present
    Basal Side Shoots: Absent

| Maturity (earliness of harvest-mature head formation): Season Application (Sharp Shooter) from # of days *1 Check (BRONCO) # of Days *1 | | |
|---|---|---|
| Spring | 70 | 72 |
| Summer | 67 | 68 |
| Fall | 70 | 71 |
| Winter | 86 | 89 |

| Planting Dates and Locations | | |
|---|---|---|
| Spring | March 21, 1996 | Saticoy, California |
| Summer | May 20, 1996 | Arroyo Grande, California |
| Fall | August 1, 1995 | Santa Maria, California |
| Winter | February 9, 1996 | Arroyo Grande, California |

*1 First water date to harvest.

Adaptation
   Primary Regions of Adaptation (tested and proven adapted)
   Southwest (California, Arizona desert): Adapted
   West Coast: Adapted
   Southeast: Not tested
   Northeast: Not tested
Season:
   Spring area—Coastal California
   Summer area—Coastal California
   Fall area—Coastal California
Greenhouse: Not tested
Soil Type: Mineral
Diseases and Stress Reactions
Virus
   Big Vein: Susceptible
   Lettuce Mosaic: Susceptible
   Cucumber Mosaic: Not tested
   Broad Bean Wilt: Not tested
   Turnip Mosaic: Not tested
   Best Western Yellows: Not tested
   Lettuce Infectious Yellows: Not tested
Fungal/Bacterial
   Corky Root Rot (Pythium Root Rot): Not tested
   Downy Mildew (Races I, IIA, III): Resistant
   Powdery Mildew: Susceptible
   Sclerotinia Rot: Susceptible
   Bacterial Soft Rot (Pseudomonas spp. & others): Not tested
   Botrytis (Gray Mold): Not tested
   Other: Corky Root Rot (Rhizomonas suberifaciens): Resistant
Insects
   Cabbage Loopers: Not tested
   Root Aphids: Not tested
   Green Peach Aphid: Susceptible
Physiological/Stress
   Tioburn: Resistant
   Heat: Intermediate
   Drought: Susceptible
   Cold: Intermediate
   Salt: Intermediate
   Brown Rib (Rib Discoloration, Rib Blight)
Post Harvest
   Pink Rib: Not tested
   Russet Spotting: Not tested
   Rusty Brown Discoloration: Not tested
   Internal Rib Necrosis (Blackheart, Gray Rib, Gray Streak): Not tested
   Brown Stain: Not tested

EXAMPLE 2

Comparison of Sharp Shooter with the Commercial Crisphead Cultivars Premier and Bronco.

Phenotypically, Sharp Shooter is distinct for its most similar group of cultivars, specifically, crisphead cultivars with corky root rot resistance. The two closest commercial crisphead cultivars widely used for crisphead production in corky root rot soils are Premier and Bronco. Premier is small to medium in size, medium to dark green in color, and often variable in uniformity, and is resistant to corky root rot. Bronco is medium to large in size, pale to medium green in color, and often variable in uniformity, and is resistant to corky root rot.

Sharp Shooter, Premier and Bronco all differ from one another in color, weight and number of plants harvested as shown in Table 1 below.

TABLE 1

Evaluation of the most similar cultivars for disease reaction, color, weight, and yield.

| Cultivar | Rep | CRR[1] | DMR[2] | Color[3] | Weight[4] | No. of Plants Harvested per 200 Plants ± SD[5] |
|---|---|---|---|---|---|---|
| Sharp Shooter | 1 | resistant | I, IIA, III, IV | 146A | 898 ± 56.7 | 169.4 ± 14.7 |
| | 2 | resistant | I, IIA, III, IV | 146A | 876 ± 54.9 | 176.0 ± 15.3 |
| Premier | 1 | resistant | I, IIA | 146A | 657 ± 39.1 | 134.4 ± 18.6 |
| | 2 | resistant | I, IIA | 146A | 687 ± 48.5 | 142.8 ± 17.6 |
| Bronco | 1 | resistant | I, IIA, III, IV | 146B | 661 ± 48.5 | 116.3 ± 22.5 |
| | 2 | resistant | I, IIA, III, IV | 146B | 615 ± 45.3 | 113.7 ± 20.1 |

[1]Survey of 50 roots per trial (two replication of 25 plants per rep per trial) obtained from plants grown in two field trials in San Luis Obispo County, CA, June 1996 and Santa Maria County, CA, August, 1996, respectively.
[2]Survey of two cotyledon tests (two replication of 25 seedlings per rep per test) of plants grown in laboratory screens at Arroyo Grande, CA, June 1996.
[3]Color evaluation was done using the Royal Horticultural Society color chart, U.K. from the leaves of plants used to determine root resistant, given above.
[4]Mean weight of 10 trimmed heads (two replication of 5 plants per rep per trial) in grams ± the standard deviation, obtained from plants grown in two field trials in San Luis Obispo County, CA, June 1996 and Santa Maria County, CA, August 1996, respectively.
[5]Mean harvest of plants from ten replications of 200 plants per cultivar ± the standard deviation, obtained from plants grown in two field trials in San Luis Obispo County, CA, June 1996 and Santa Maria County, CA, August, 1996, respectively.

What is claimed is:

1. *Lactuca sativa* seed designated as Sharp Shooter having ATCC Accession No. 209461.

2. A *Lactuca sativa* plant produced by growing the seed of claim 1.

3. A *Lactuca sativa* plant having all the physiological and morphological characteristics of the Lactuca sativa plant of claim 2.

4. A $F_1$ hybrid *Lactuca sativa* plant having Sharp Shooter as a parent, wherein Sharp Shooter is grown from seed having ATCC Accession No. 209461.

* * * * *